United States Patent [19]

Golden

[11] Patent Number: 4,676,256

[45] Date of Patent: Jun. 30, 1987

[54] HYPODERMIC DEVICE

[76] Inventor: Theodore A. Golden, 762 Wooddale Rd., Birmingham, Mich. 48010

[21] Appl. No.: 843,275

[22] Filed: Mar. 24, 1986

[51] Int. Cl.4 .............................................. A61B 5/00
[52] U.S. Cl. .................................... 128/762; 128/763; 604/148; 604/191; 604/244; 604/249
[58] Field of Search ............... 604/148, 187, 191, 232, 604/244, 249; 128/760, 762, 763, 764, 765, 766

[56] References Cited

U.S. PATENT DOCUMENTS 3,405,706 10/1969 Cinqualbre ........................... 128/762
3,494,351 6/1970 Horn ................................... 128/762

Primary Examiner—William E. Kamm
Assistant Examiner—Randy Citrin
Attorney, Agent, or Firm—Cullen, Sloman, Cantor, Grauer, Scott & Rutherford

[57] ABSTRACT

A hypodermic device including a main body having a plurality of open sockets with a corresponding number of upstanding needles therein. In one embodiment, each upstanding needle is commonly interconnected to a main passage through the body. The ends of the upstanding needles are capped with resilient plugs which are displaced when one or more vacuum tubes are pressed onto the ends of the upstanding needles. In an alternative embodiment of the device, the upstanding needles are secured to movable plugs with each plug having a passage therein which is selectively movable into coaxial alignment with the main passage through the body. In yet another embodiment of the device, the sockets are spaced apart along the length of the main body with valves being connected to the main body in the spaces between the sockets. Each valve is slidably movable within a well formed within the body. A passage through each valve is brought into coaxial alignment with the main passage through the body thereby permitting blood to be drawn into one or more of the vacuum tubes.

6 Claims, 7 Drawing Figures

HYPODERMIC DEVICE

BACKGROUND OF THE INVENTION

The present invention relates to a hypodermic device having multiple sockets or receptacles to permit the simultaneous extraction of blood into several tubes or containers.

It is conventional to use hypodermic devices for extracting blood for testing. In a conventional hypodermic syringe, the needle is inserted into a vein and a plunger is pulled or retracted to create a vacuum inside the syringe that causes blood to flow through the needle and into the body of the syringe. In another type of hypodermic device, a vacuum tube is pressed onto an end of the needle with the other end of the needle being inserted into the vein. The vacuum within the tube draws the blood through the needle and into the tube.

Known hypodermic devices, however, suffer shortcomings. More than one tube of blood is normally required for the multitude of tests being conducted today by physicians. If a conventional hypodermic syringe is used, this means that after one syringe is filled and removed, another syringe must be inserted into the vein. Multiple extractions result in more discomfort to the patient, added difficulty for the person extracting the blood, and the increased possibility of disease transmission. Similarly, when the other type of hypodermic device is used, the operator must steady the device while a filled vacuum tube is removed and then attach another vacuum tube to the hypodermic needle. Again, similar problems occur as with the first type of hypodermic device.

Thus, it is the principal object of the present invention to eliminate the deficiencies of the prior hypodermic devices by providing a mechanically simple, low cost, light weight, hypodermic device that has multiple sockets thereby permitting multiple simultaneous extractions of blood into a plurality of tubes.

SUMMARY OF THE INVENTION

The invention contemplates a device including a main body or carrier having a plurality of open sockets or containers which may be integrally fabricated with the main body. Each socket has an upstanding needle therein with each of the needles being commonly interconnected to a main passage through the carrier. The upstanding needles are arranged such that their axes are generally perpendicular to the main passage. Further, the needles may be made of metal, plastic or other materials capable of piercing through a rubber seal, as will be described. Moreover, the needles may be integrally fabricated with the main passage or attached thereto as separate parts.

The main passage through the carrier extends outwardly of the carrier through a male threaded fitting. A hypodermic needle having an internally threaded female end is attached to the fitting. Thus, when the hypodermic needle is inserted into a patient's vein, blood passes through the hypodermic needle, the main passage, and into the upstanding needles.

The sockets are disclosed as having a generally circular cross-section. However, other cross-sections are possible including oval, polygonal and the like. An oval cross-section for the sockets, for example, provides the advantage of a narrower or shorter carrier thereby making it easier to handle.

In one embodiment, the ends of the upstanding needles are capped with resilient plugs prior to using the hypodermic device. This prevents contaminants from entering into the upstanding needles and maintains sterility. The plugs may be made of any material that is flexible enough to permit piercing by the sharp ends of the upstanding needles without blocking the passage of blood through the needles.

When it is desired to extract blood from a patient, the hypodermic needle is inserted into the patient's vein with one or more vacuum tubes thereafter being pressed downwardly onto the end of a respective upstanding needle. Each vacuum tube has a rubber cover or seal over the open end thereof which is pierced by the end of the upstanding needle when the vacuum tube is pressed downwardly into a socket. The downward movement of the vacuum tube also displaces or pushes the resilient plug downwardly toward the bottom of the socket, thereby permitting blood to flow into the vacuum tube through the upstanding needle.

In another embodiment of the invention, the upstanding needles are secured to movable plugs with each plug having a passage therein which is selectively movable into coaxial alignment with the main passage through the carrier. Each upstanding needle is interconnected to a respective passage through the plug with the axis of the needle being substantially perpendicular to the axis of the passage. When a plug is pushed downwardly, it finally bottoms out within a socket such that the passage through the plug is automatically brought into coaxial alignment with the main passage through the carrier.

In the inoperative position of the plug, the interior wall of the socket blocks both ends of the passage through the plug and a solid portion of the plug blocks the main passage. Further, to prevent contamination from entering the upstanding needles, caps are provided to cover the open ends of the sockets with the caps being conveniently removable.

When it is desired to extract blood using the second embodiment of the hypodermic device, the hypodermic needle is inserted into the patient's vein, and thereafter, one or more vacuum tubes are pushed downwardly into the sockets. The downward movement of a vacuum tube pushes a respective plug toward the bottom of the socket until it bottoms out thereby bringing the passage through the plug into coaxial alignment with the main passage through the carrier. This permits blood to be drawn into the vacuum tube with each successive section of the main passage being blocked by a bottom section of the next movable plug.

In yet another embodiment of the hypodermic device of the present invention, the sockets in the carrier are spaced apart along the length of the carrier with valves being connected to the carrier in the spaces between the sockets. Each valve is slidably movable within a well formed within the carrier. A passage through the valve is brought into coaxial alignment with the main passage through the carrier. When the valves are in their retracted or inoperative position, their end portions block the main passages through the carrier. To extract blood, one or more vacuum tubes are pushed downwardly into the sockets with all of the valves being retracted and the hypodermic needle is then inserted into the patient's vein. Thereafter, one or more of the valves are successively pressed inwardly into the carrier until its end portion bottoms out which automatically brings the passage through the valve into coaxial alignment with the main passage through the carrier. This permits blood to be drawn into one or more of the vacuum tubes.

Other advantages and meritorious features of the present invention will be more fully understood from the detailed description of the invention, the appended claims, and the drawings, which are briefly described hereinbelow.

DETAILED DESCRIPTION OF THE INVENTION

Figure 1:
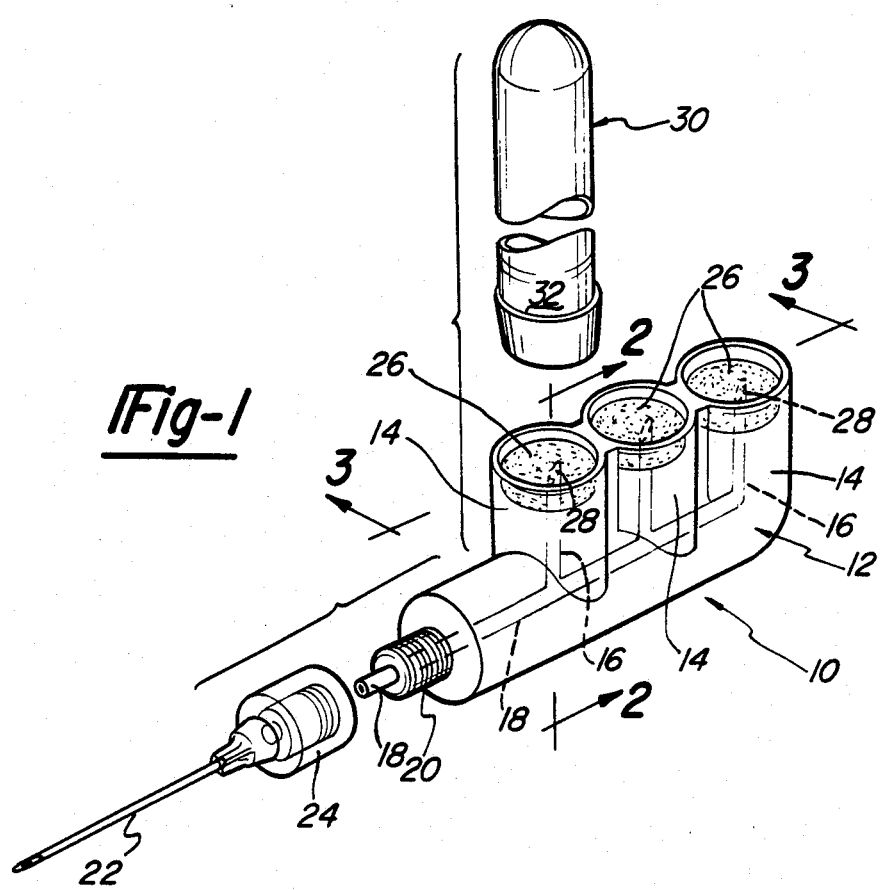
FIG. 1 is a perspective side view of the hypodermic device of the present invention.
Figures 2, 3:
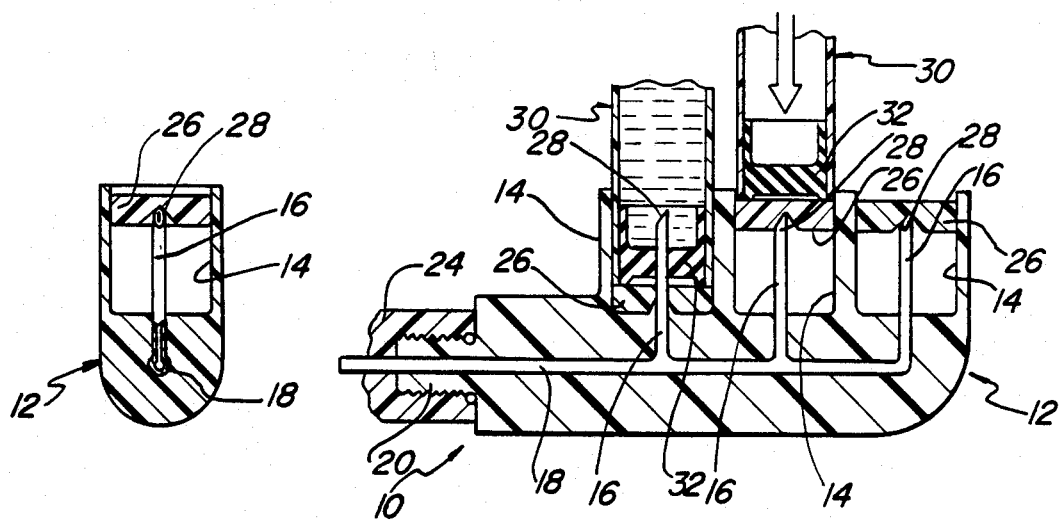
FIG. 2 is a cross-sectional view taken along line 2—2 in FIG. 1.
FIG. 3 is a cross-sectional view taken along line 3—3 in FIG. 1.

FIGS. 1-3 illustrate an improved hypodermic device 10 made in accordance with the teachings of the present invention. Device 10 includes a main body or carrier 12 having a plurality of open sockets or containers 14, which may be integrally fabricated with the main body or manufactured as separate parts. Each socket has an upstanding needle 16 therein with each of the needles 16 being commonly interconnected to the main passage 18 through body 12. Needles 16 are arranged such that their axes are generally perpendicular to passage 18. Further, needles 16 may be made of metal, plastic or other materials capable of piercing through a rubber seal as will be described. Moreover, needles 16 may be integrally fabricated with main passage 18 or attached thereto as separate parts.

Passage 18 extends outwardly of carrier 12 through a male threaded fitting 20. A hypodermic needle 22 having an internally threaded female end 24 is attached to fitting 20. Thus, when needle 22 in inserted into a patient's vein, blood passes through needle 22, main passage 18, and into needles 16.

Sockets 14 are illustrated as having a generally circular cross-section in FIGS. 1-3. It will be apparent to those skilled in the art that other cross-sections are possible including oval, polygonal and the like. An oval cross-section for sockets 14, for example, would provide the advantage of a narrower or shorter carrier 12 thereby making it easier to handle.

The ends of needles 16 are capped with resilient plugs 26 prior to using hypodermic device 10. This prevents contaminants from entering needles 16 and maintains sterility. Plugs 26 may be made of any material that is flexible enough to permit piercing by the sharp ends 28 of needles 16 without blocking the passage of blood through the needles.

When it is desired to extract blood from a patient, the hypodermic needle 22 is inserted into the patient's vein with one or more vacuum tubes 30 thereafter being pressed downwardly onto the ends 28 of a respective needle 16 as shown in FIG. 3. Each vacuum tube 30 has a rubber cover or seal 32 over the open end thereof which is pierced by needle end 28 when tube 30 is pressed downwardly into socket 14. The downward movement of tube 30 also displaces or pushes plug 26 downwardly toward the bottom of socket 14, thereby permitting blood to flow into a tube 30 through needle 16.

Tubes 30 have a pre-existing amount of vacuum therein which will automatically cause blood to be drawn into them when the seal 32 is pierced by needle 16. Thus, the operator simply inserts the hypodermic needle 22 into the patient's vein and thereafter extracts the desired amount of blood by successively pressing vacuum tubes 30 down into sockets 14 onto needle 16.

Figure 4:
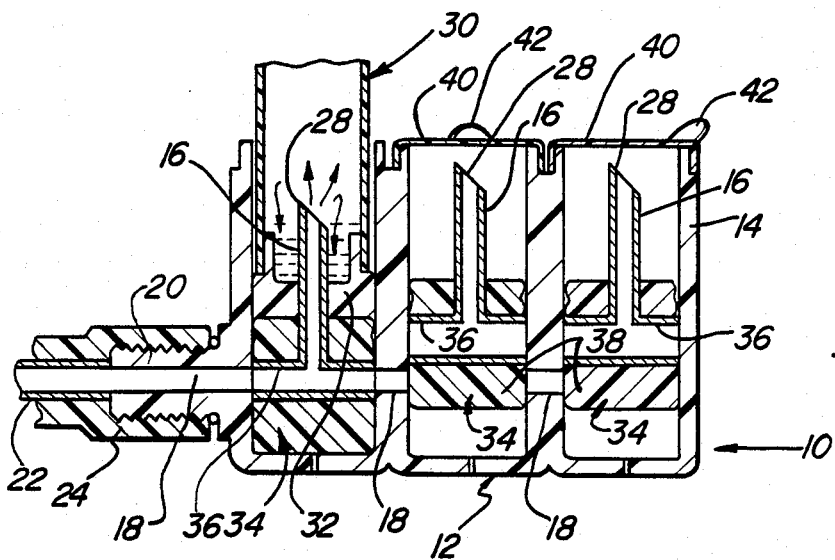
FIG. 4 is a cross-sectional side view of an alternative embodiment of the device including movable plugs.

FIG. 4 illustrates an alternative embodiment of the hypodermic device 10 wherein needles 16 are secured to movable plugs 34. Each plug 34 includes a passage 36 therein which is selectively movable into coaxial alignment with the main passage 18 through body 12. Body or carrier 12 again includes a plurality of open sockets 14 with plugs 34 being slidably movable therein. Each needle 16 is interconnected to the passage 36 through plug 24 with the axis of a needle 16 being substantially perpendicular to the axis of a passage 36. When plug 34 is pushed downwardly, as illustrated in the left-most socket 14 of FIG. 4, it finally bottoms out within socket 14 such that passage 36 is automatically brought into coaxial alignment with main passage 18.

The inoperative position of plug 34 is shown to the right in FIG. 4 wherein the interior wall of socket 14 blocks both ends of passage 36 and the lower solid portion 38 of plug 34 blocks main passage 18. To prevent contamination from entering needles 16 when not in use, caps 40 are provided to cover the open ends of sockets 14. Caps 40 may be conveniently removed by pulling on tabs 42.

When it is desired to extract blood, hypodermic needle 22 is inserted into the patient's vein, and thereafter, one or more vacuum tubes 30 are pushed downwardly into sockets 14. The downward movement of a tube 30 pushes plug 34 toward the bottom of socket 14 until it bottoms out thereby bringing passage 36 into coaxial alignment with main passage 18. This permits blood to be drawn into tube 30 through passage 18, passage 36, and needle 16 due to the vacuum within tube 30. Moreover, each successive section of main passage 18 is blocked by the bottom section 38 of the next plug 34.

Figure 5:
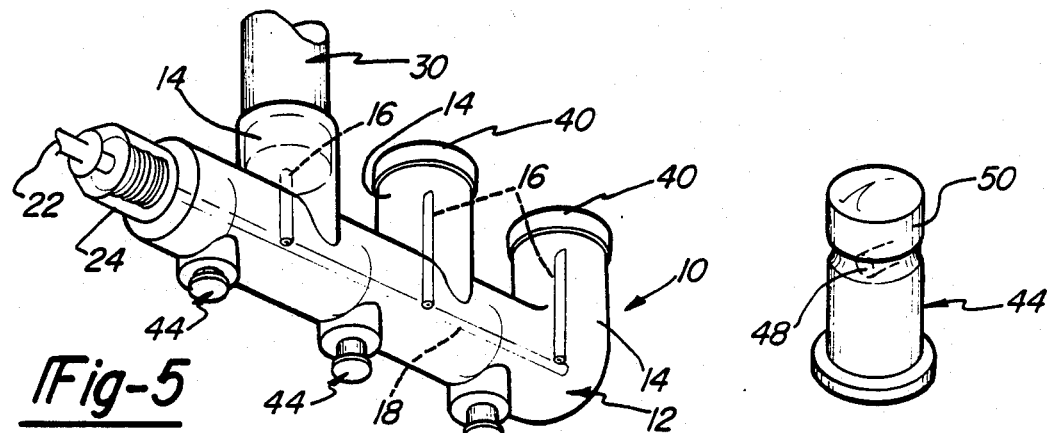
FIG. 5 is a perspective view of yet another embodiment of the hypodermic device of the present invention.
Figure 7:
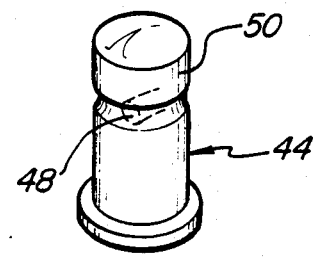
FIG. 7 is a perspective view of one of the valves utilized in the device illustrated in FIG. 5.
Figure 6:
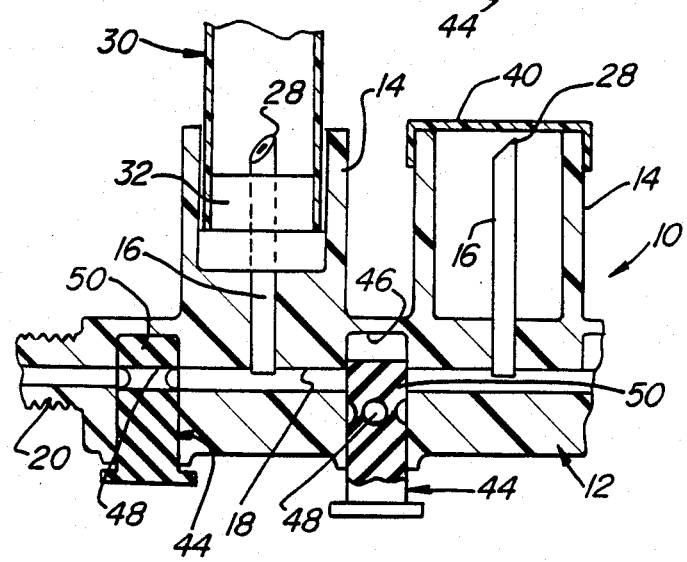
FIG. 6 is a cross-sectional side view of the device illustrated in FIG. 5.

FIGS. 5-7 illustrate yet another embodiment of the hypodermic device 10 wherein a plurality of valves 44 are utilized. In this embodiment, sockets 14 are spaced apart along the length of carrier 12 with valves 44 being connected to carrier 12 in the spaces between sockets 14. Each valve 44 is slidably movable within a well 46 formed within carrier 12. A passage 48 through valve 44 is brought into coaxial alignment with main passage 18 as follows.

Valve 44 is in a retracted or inoperative position as shown to the right in FIG. 6 such that its end portion 50 blocks passage 18. To extract blood, one or more vacuum tubes 30 are pushed downwardly into sockets 14 with all of the valves 44 being retracted, and then, needle 22 is inserted into the patient's vein. Thereafter, one or more of the valves 44 are successively pressed inwardly into body 12 until its end portion 50 bottoms out in well 46 which automatically brings passage 48 into coaxial alignment with passage 18. This permits blood to be drawn into one or more tubes 30 through passage 18, passage 48 and needle 16 due to the vacuum within each tube 30.

With this detailed description of the hypodermic device of the present invention and the opertion thereof, it will be obvious to those skilled in the art that various modifications can be made to the hypodermic device and in the materials and specific configurations used therein without departing from the spirit and scope of the present invention which is limited only by the appended claims.

I claim:

1. A device for extracting blood comprising:
   a main body having a plurality of sockets with each socket having a needle therein with the longitudinal axis of each of the needles being substantially parallel to the longitudinal axis of each respective socket;
   an axially movable plug coaxially mounted within each socket adjacent an end of each needle;
   means interconnecting each of said needles to a main passage through said body;
   a hypodermic needle connected to said main passage; and
   one or more tubes, each having a sealed end with a predetermined amount of vacuum therein with each tube being operatively inserted into a selected socket for piercing the sealed end of the tube with a needle end and with the movable plug being axially displaced by the movement of the tube within the socket.

2. The blood extracting device as set forth in claim 1 wherein the longitudinal axis of each needle is substantially perpendicular to the longitudinal axis of said main passage.

3. A device for extracting blood comprising:
   a main body having a plurality of sockets with each socket having a needle therein with the longitudinal axis of each of said needles being substantially parallel to the longitudinal axis of each respective socket;
   means interconnecting each of said needles to a main passage through said body, said interconnecting means comprising a movable plug within each socket having a passage therein which is selectively movable into coaxial alignment with the main passage and each needle connected to a respective plug passage;
   a hypodermic needle connected to said main passage; and
   one or more tubes each having a sealed end with a predetermined amount of vacuum therein and each tube being operatively inserted into a selected socket with the sealed end of the tube being pierced by a respective needle within the socket thereby permitting fluid communication between said hypodermic needle and the tube.

4. The blood extracting device as set forth in claim 1 wherein the longitudinal axis of each needle being substantially perpendicular to the longitudinal axis of said main passage.

5. The blood extracting device as set forth in claim 1 with each plug being movable to a first position wherein the ends of the plug passage are blocked by an interior wall of a respective socket and a portion of the plug blocking the main passage, and each plug being movable to a second position wherein the plug passage is coaxially aligned with the main passage.

6. The blood extracting device as set forth in claim 5 wherein the axis of each needle being substantially perpendicular to the axis of a respective plug passage.

* * * * *